United States Patent [19]

Esrig et al.

[11] Patent Number: 5,640,237
[45] Date of Patent: Jun. 17, 1997

[54] METHOD AND APPARATUS FOR DETECTING NON-UNIFORMITIES IN REFLECTIVE SURAFACES

[75] Inventors: Paul Esrig, Saratoga; Eric James Hansotte, Sunnyvale, both of Calif.

[73] Assignee: KLA Instruments Corporation, San Jose, Calif.

[21] Appl. No.: 521,240

[22] Filed: Aug. 29, 1995

[51] Int. Cl.⁶ .................................................. G01N 21/88
[52] U.S. Cl. ................................................................. 356/237
[58] Field of Search ................................. 356/394, 237

[56] References Cited

U.S. PATENT DOCUMENTS

| | | | |
|---|---|---|---|
| 4,695,157 | 9/1987 | Schoenbaum et al. | 356/237 |
| 4,972,093 | 11/1990 | Cochran et al. | 356/394 |
| 5,392,113 | 2/1995 | Sayka et al. | 356/237 |

Primary Examiner—Richard A. Rosenberger
Attorney, Agent, or Firm—Claude A. S. Hamrick

[57] ABSTRACT

Method and apparatus for detecting non-uniformities in reflective surfaces, including an electro-luminescent panel for providing a substantially uniform illumination of the reflective surface of a planar object, such as a silicon wafer to be inspected, a camera positioned at an angle suitable for detecting light reflected from the inspected surface and for generating an output representative of the intensity of light reflected from each pixel of the reflective surface, and processing apparatus communicatively coupled to the camera and responsive to the output generated by the camera to in turn generate an output indicative of the surface uniformity of the surface under inspection. The preferred embodiment will normally include an appropriate housing or baffle structure for limiting the light viewed by the camera to that from the source as reflected by the surface being inspected, and may further include wafer-handling means and camera-positioning means.

22 Claims, 6 Drawing Sheets

METHOD AND APPARATUS FOR DETECTING NON-UNIFORMITIES IN REFLECTIVE SURAFACES

BACKGROUND OF THE INVENTION

1. Field of the Invention

The present invention relates generally to apparatus for detection of irregularities in reflective surfaces, and more particularly to an automated method and apparatus for inspecting planar objects such as silicon wafers, painted or polished surfaces, etc., to detect surface non-uniformities.

2. Description of the Prior Art

With increasing demand for integrated circuit devices, manufacturing efficiency and yield become more and more important. In the fabrication of integrated circuits on silicon wafers, a large number of integrated circuits are simultaneously processed during multi-stage operations generally referred to as wafer fabrication or wafer processing. Upon completion of the processing operation, the individual integrated circuits are tested and marked as either acceptable or unacceptable. The wafer is then fractionated into dice or chips, each of which contains one of the integrated circuits, and the chips which have passed inspection are packaged to provide usable IC devices. However, numerous processing steps are required during the wafer processing operation, and during any step process variations may occur which can result in irregularities that materially affect the yield of the wafer. It is therefore desirable to have means available for inspecting the wafer at various points during the processing sequence so that system faults can be discovered and abated, and ultimately, yield optimized.

In general, the geometry of the various integrated circuit components formed in the wafer surface are defined by a photolithographic process wherein an oxide layer is initially grown on the wafer surface, a thin layer of photo-sensitive resist material is deposited over the oxide layer, and the resist layer is exposed to high-intensity ultraviolet light through a pattern mask which defines (1) areas of the wafer which will remain covered or masked and (2) areas which will be uncovered during subsequent processing steps, which might include coating by various means such as spin-coating, deposition (CVD), and etching by various means including the application of chemical etching and plasma etching techniques. These processes are normally repeated a number of times during the fabrication of a silicon wafer to develop the multiple layers of integrated circuit components. It is not unusual for a silicon wafer to undergo 20 or more processing iterations before the fabrication operation is completed.

A problem that may occur during any of the several coating and etching steps is that of resist-burning of the wafer surface. The actual cause of resist-burning is not completely understood, but the factors that contribute include (1) non-uniform cooling of the wafer, (2) uneven flow of gas in the processing chamber, (3) non-uniform or incorrect temperature of the processing chamber, (4) non-uniform cooling under the wafer, and (5) variations in voltage during processing. Such resist-burning causes inconsistent patterning of integrated circuit components and distortion of line width formations in the burned regions. When resist burns occur, it is not uncommon to find regions of the wafer in which line widths of, for example, 0.5μ may be distorted to as much as 0.8μ. The inconsistent patterning and distorted line widths that result may affect circuit operation and may even render the integrated circuits formed in the burned regions to be inoperable.

Heretofore, silicon wafers have been visually inspected for resist burns. At certain light reflection angles, resist burn regions of a wafer appear darker than normal regions that are not resist-burned. To inspect a wafer, an operator would typically pick up the wafer with tweezers, reflect light off the surface, and look for regions which were discolored or experienced irregular reflection. However, such visual inspections are not reliable and normally are not specific enough to allow any more than a gross GO or NO-GO decision to be made. When a resist-burned region is found, the operator may elect to mark the region or discard the wafer entirely. If the wafer is not discarded, it is important to mark the defective regions because later processing steps may mask the burned region or regions so that the defective portions of the wafer will appear normal upon later inspection.

In an attempt to prevent resist burns, processing equipment has heretofore been periodically inspected and carefully maintained. For instance, before a work shift, a processing chamber may be taken off line to run test wafers. After the test wafers are processed, they are examined at the microscopic level, and line width measurements may be taken to ensure proper operation of the processing chamber. After verification, the chamber is then placed back on line to process actual production wafers, but this verification process may take as much as an hour or more of time that could otherwise be spent processing the wafers. Since no devices are commercially available for detecting resist burns on the production line, off-line verification of the processing equipment is the best technique available for reducing the occurrence of the resist-burning phenomena and thus avoiding substantial reductions in yield of processed wafers.

It is therefore desirable that in-line inspection apparatus be provided for automatically inspecting and detecting the resist burns on silicon wafers occurring during the production process.

SUMMARY OF THE INVENTION

A principal objective of the present invention is thus to provide an apparatus for automatically detecting surface non-uniformities on reflective surfaces.

Another objective of the present invention is to provide an apparatus which can detect resist burns on silicon wafer surfaces during the production process.

Yet another objective of the present invention is to provide an apparatus for detecting surface non-uniformities as indicators of resist burns.

Still another objective of the present invention is to provide an automated detection apparatus for detecting resist burns on silicon wafers.

Briefly, a preferred embodiment of the present invention includes an electro-luminescent panel for providing a substantially uniform illumination of the reflective surface of a planar object, such as a silicon wafer to be inspected, a camera positioned at an angle suitable for detecting light reflected from the inspected surface and for generating an output representative of the intensity of light reflected from each pixel of the reflective surface, and processing apparatus communicatively coupled to the camera and responsive to the output generated by the camera to in turn generate an output indicative of the surface uniformity of the surface under inspection. The preferred embodiment will normally include an appropriate housing or baffle structure for limiting the light viewed by the camera to that from the source as reflected by the surface being inspected, and may further include wafer-handling means and camera-positioning means.

An important advantage of the present invention is that it provides a novel mechanism for automatically detecting resist burns on silicon wafers during the wafer fabrication process.

Another advantage of the present invention is that it can be used to inspect wafers following any stage of the fabrication process.

These and other objects and advantages of the present invention will no doubt become apparent to those skilled in the art after having read the following detailed description of the preferred embodiment which is illustrated in the several figures of the drawing.

IN THE DRAWING

BRIEF DESCRIPTION OF THE PREFERRED EMBODIMENT

Figure 1:
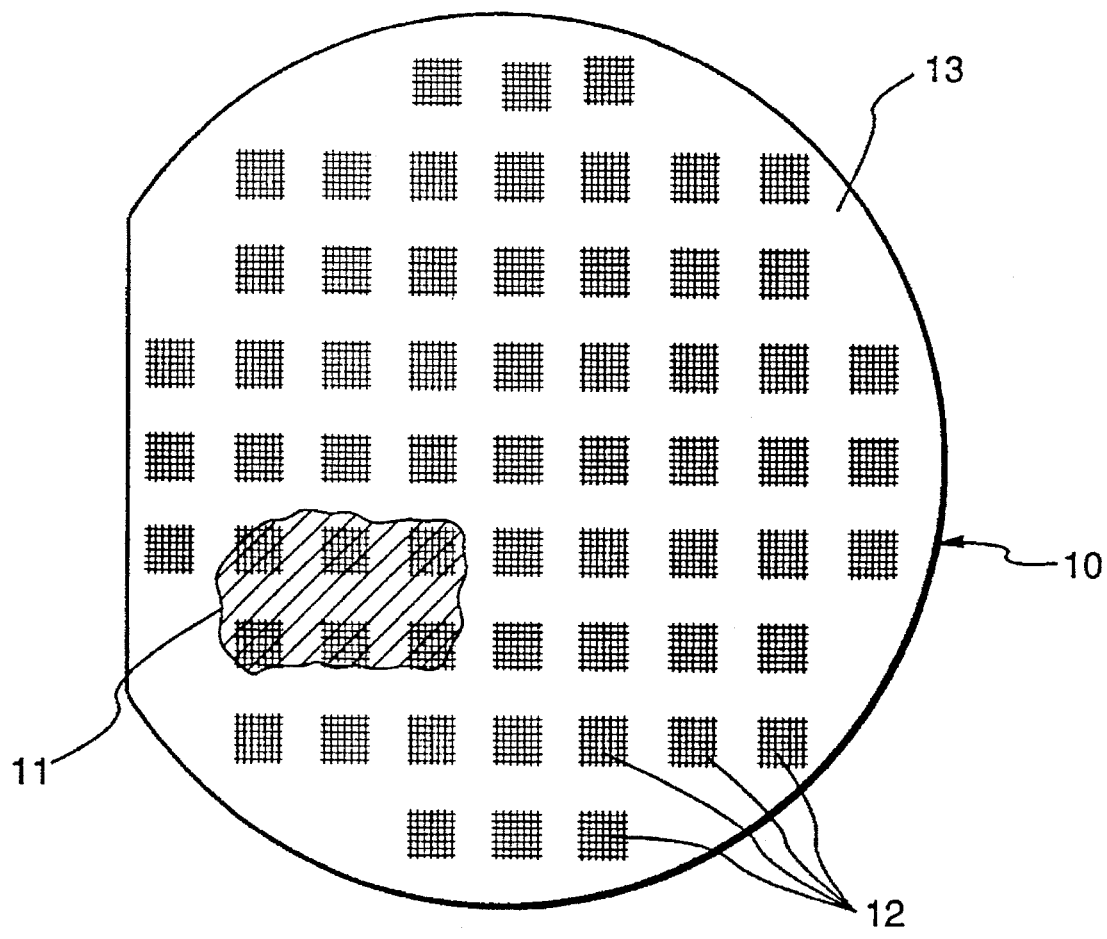
FIG. 1 is a plan view showing the processed surface of a silicon wafer having at least one resist-burned region.

Referring now to the drawing, FIG. 1 is a plan view showing the processed side of a silicon wafer 10, including a plurality of integrated circuits 12 partially or fully formed in the wafer surface 13. Ideally, the reflectivity of the wafer surface is uniform over the entire wafer with the exception, of course, that the characteristics of each IC will cause an image thereof to be reflected. However, since each IC 12 is identical, the reflected image of each IC should be identical. (Note, however, that a few of the IC sites may be reserved as fiducials for alignment purposes.) But, if one or more regions of the surface have a different reflectivity from that of the rest of the wafer surface, such difference may indicate that the wafer has experienced resist burns during one or more stages of its processing.

One such non-uniform region is depicted at 11 in FIG. 1. This region may be dramatically apparent to the naked eye, or it may have but a subtle difference in reflective characteristics. But in either case, the burned region may have experienced damage that can affect the reliability or even operability of any ICs formed within the region. The size, number, and location of such non-uniform areas cannot be predicted, and such regions can occur anywhere on the wafer surface.

Figure 2:
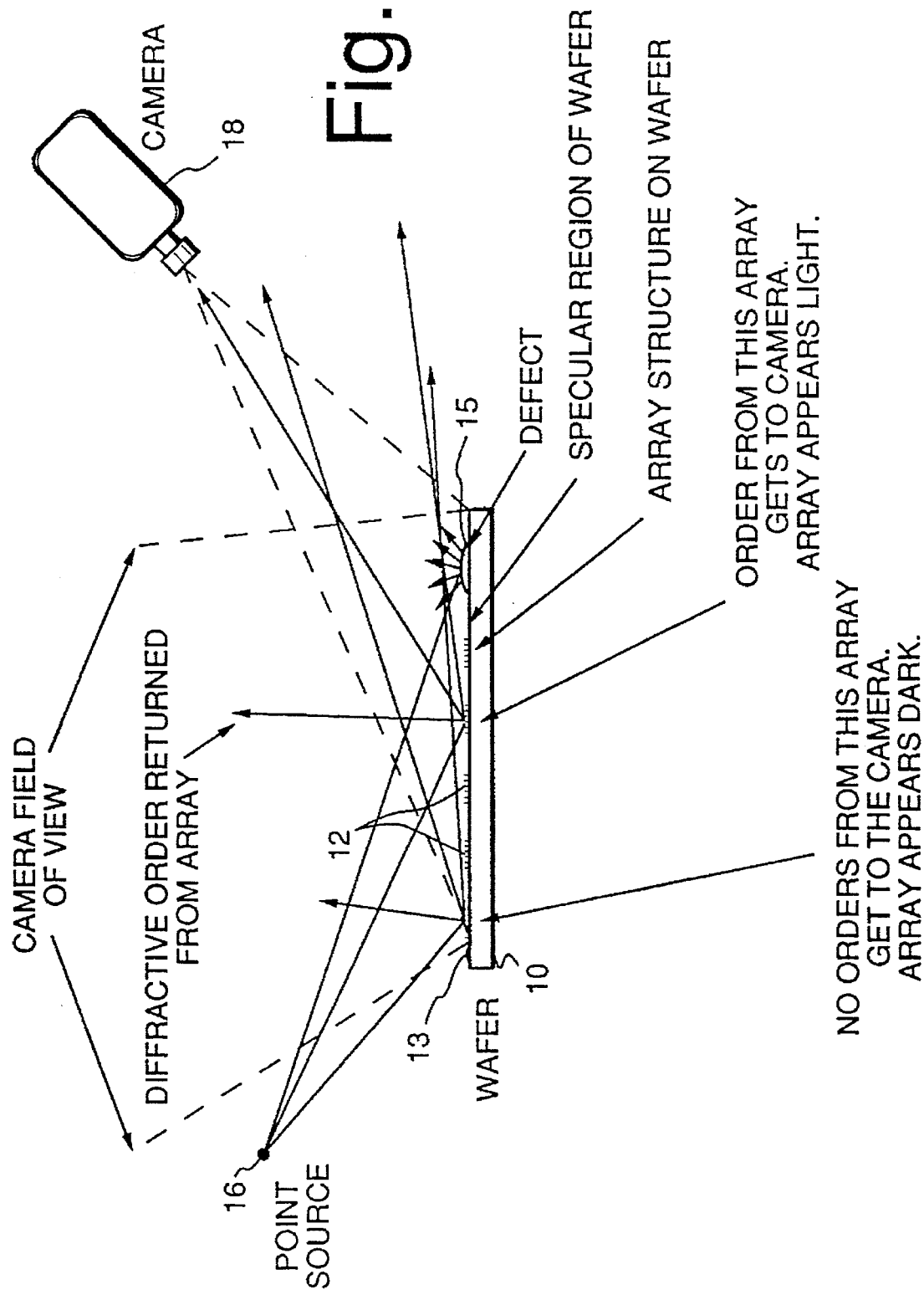
FIGS. 2 and 3 are diagrams used to distinguish the present invention from unworkable approaches.

If, as depicted in FIG. 2 of the drawing, one were to attempt inspection of the surface 13 of a wafer 10 using a point source of light 16 and a scanning electronic camera 18, the IC structures 12 previously etched into the wafer surface (usually periodic arrays of various types of circuit components) will act as diffraction gratings which will cause directional diffractive orders to be returned from the wafer surface when point sources or other localized regions of illumination are used. Such illumination causes bright bands to appear on an otherwise dark wafer surface. Regions where an order gets returned to the camera aperture appear bright, and those where an order misses the aperture appear dark. Specular regions of the wafer appear dark because they only reflect the zero order, and since the source is outside the camera field of view, this order never reaches the camera aperture. Defects 15 appear bright because they scatter light in all directions. This point source type of illumination is thus undesirable because it would be impossible to discern defects from the bright bands caused by diffractive effects, since both would appear bright on the dark wafer background. Note that the camera must be outside its reflected field of view so that it does not see its own reflection.

Figure 3:
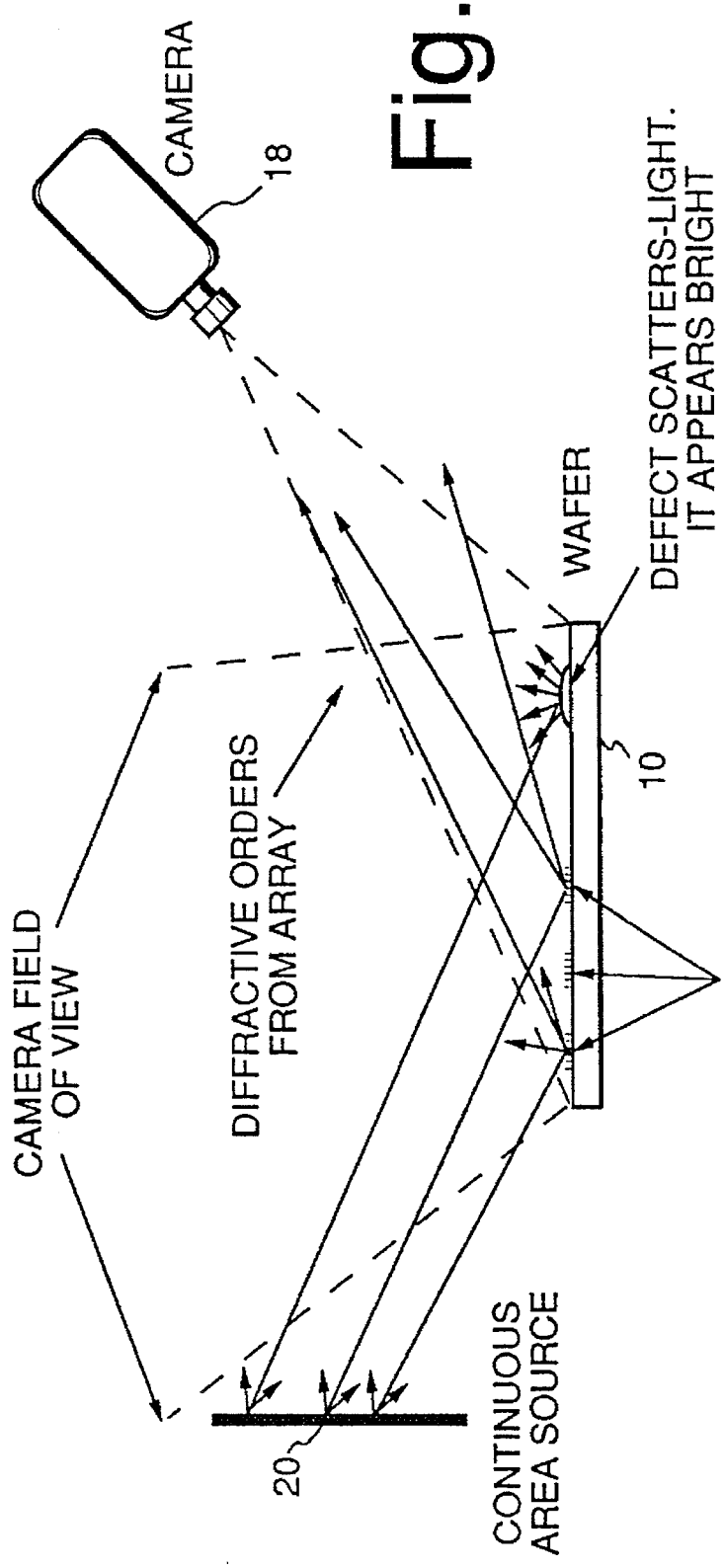

If, instead of using a point source of light, an extended area source 20 is used as depicted in FIG. 3 of the drawing, the problem of distinct directional orders will be resolved because they get smoothed out, so to speak, since the area source is essentially a collection of an infinite number of point sources spaced infinitely close together. The reflected orders from the infinity of points overlap each other so that all of the little array structures return some light and appear lit. There are no bright bands. Thus, when the area source is used outside the camera field of view, as a kind of dark field, the wafer array structure 12 and the defects 15 appear bright since they return diffractive orders and scattered light respectively to the camera 18. But specular areas of the wafer still appear dark since their reflected light misses the camera aperture. This type of illumination is again undesirable because the camera sees bright array patterns and defects against the dark specular background of the wafer, and it is hard for image processing to distinguish the defects from the IC arrays.

Figure 4:
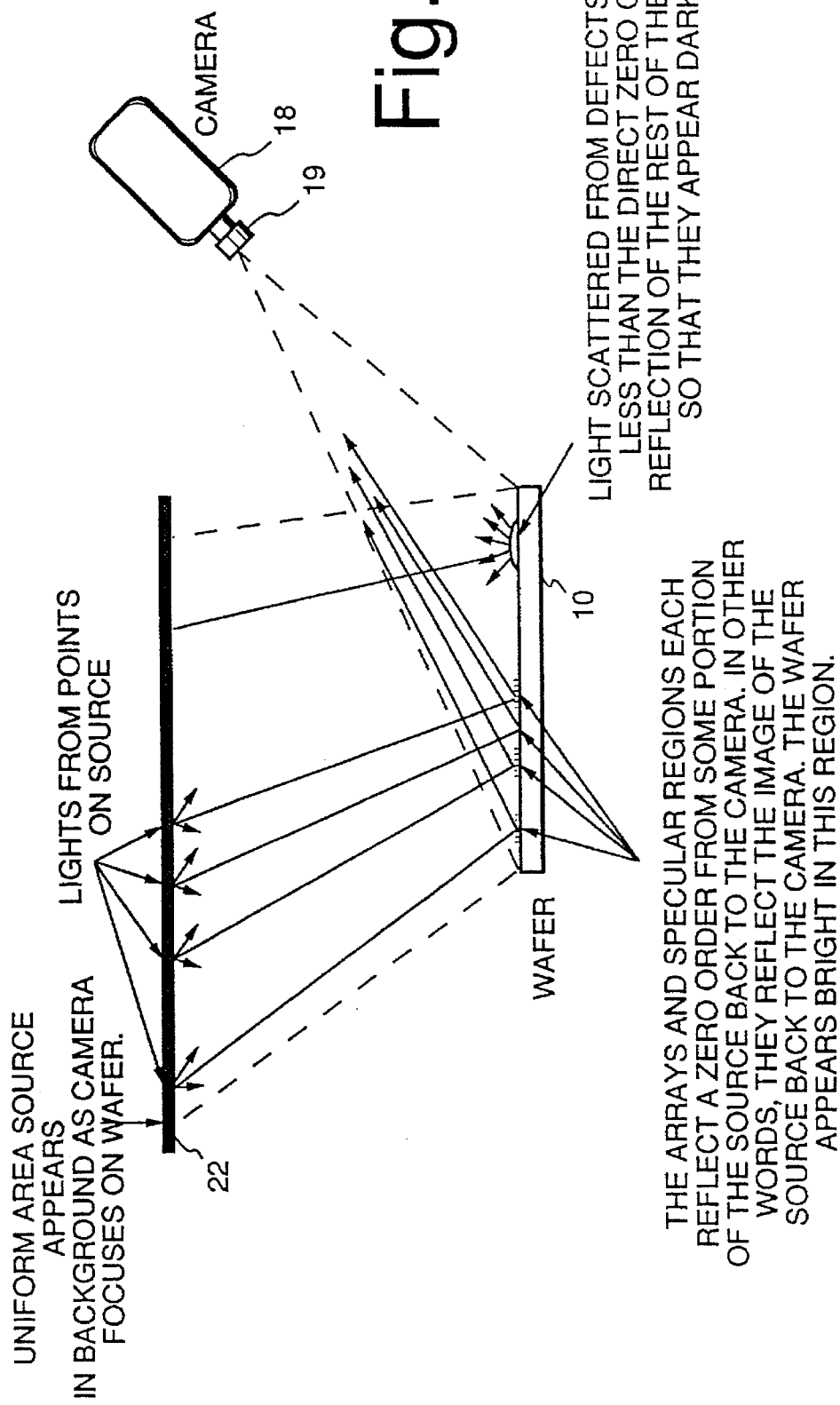
FIG. 4 is a diagram conceptually illustrating the light-illuminating and gathering components of the present invention.

However, when, as depicted in FIG. 4, an area source 22 is placed inside the field of view of the camera 18 (as reflected by wafer 10), then the entire wafer appears bright except for defects. This is because both the specular areas and the array structures reflect the zero or specular orders back into the camera aperture. The defects scatter light so that less light gets to the camera relative to the arrays and specular portions of the wafer, and they appear materially darker.

Another way to view this effect is that the camera 18 sees the reflection of the uniform source 22 in the wafer. As the camera focuses on the wafer, the image of the source appears in the background reflected by the wafer. Scratches or defects in the wafer obstruct the image of the uniform source, and appear as darker regions. One skilled in the art will remember that often in microscope-like instruments it is possible to check for dust or scratches on lens or mirror surfaces within the optical system by focusing on those surfaces instead of the object plane. Meanwhile, an object of uniform brightness is illuminated in the object plane so that dust on the focused surface appears against a uniform background and is therefore easy to recognize. Within this analogy, the wafer 10 is simply a folding mirror in an optical system consisting of the source 22 (in the object plane), wafer 10, lens 19, and a CCD array in the image plane of camera 18. Camera lens focus is then adjusted to look for defects or particles on the wafer which appear against the uniform but out-of-focus object.

In accordance with the present invention, if the wafer 10, or other object to be inspected, is reflective but does not have periodic diffractive structures, then the problem of the diffractive orders will not exist. In such case, the object could be illuminated with point sources like the one illustrated in FIG. 2. If the object were not specularly reflective (like a piece of wood or paper), then one would be even less constrained in that he would have neither the problem of the source image being specularly reflected directly into the camera, nor the camera seeing its own reflection in the wafer. Thus, unlike the situation in FIG. 2, the source could be located anywhere so long as it was not in the direct path between the camera and the object, and the camera could lie in the space above the wafer without seeing its own reflection.

Figure 5:
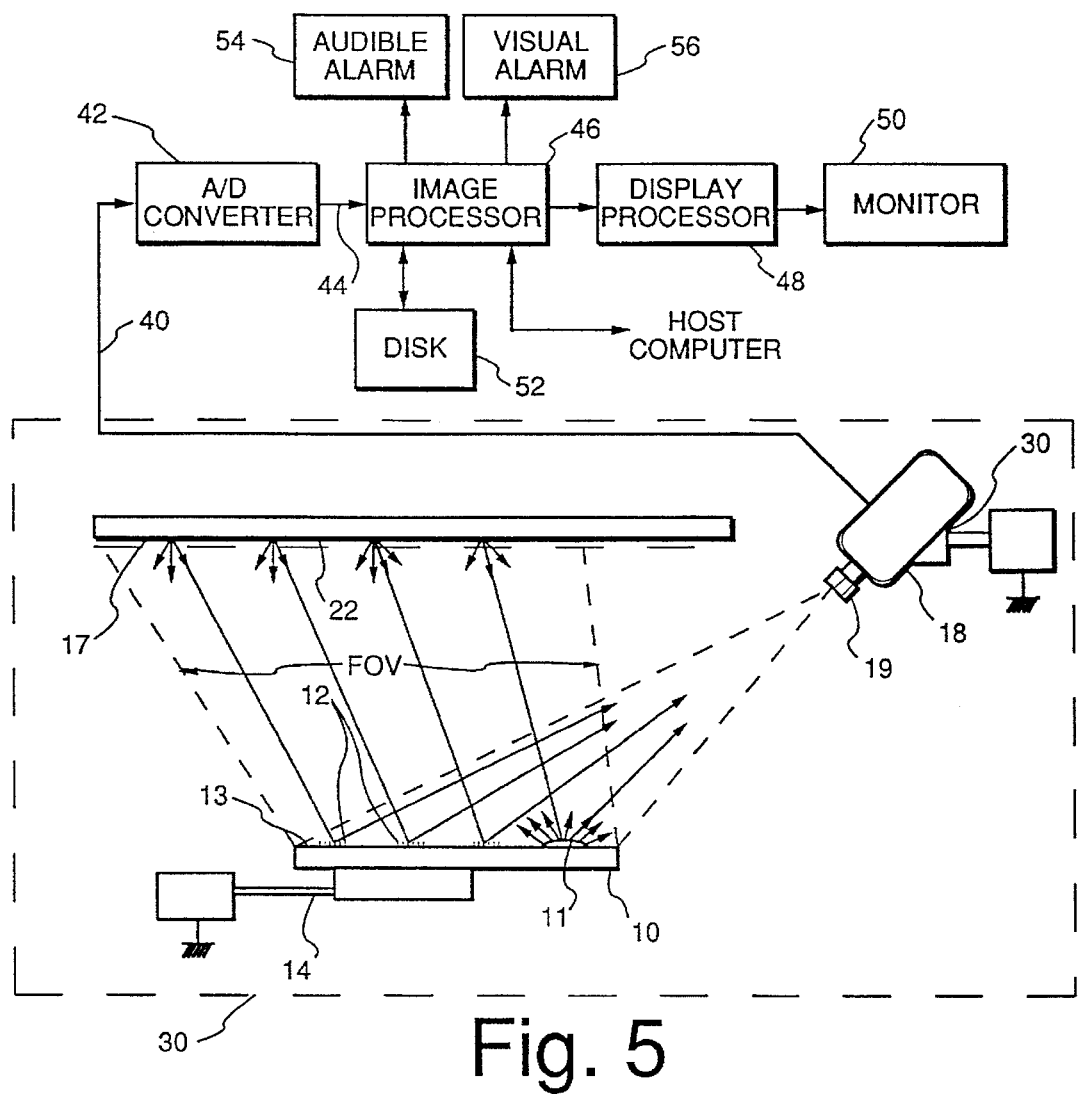
FIG. 5 is a diagram schematically illustrating a preferred embodiment of the present invention.

Referring now to FIG. 5, a simplified schematic and block diagram of a preferred embodiment of the present invention, implementing the concept of FIG. 4, is illustrated for detecting wafer areas 13 of non-uniform reflectivity. Disposed within a suitable housing or shroud 30 is a wafer transport mechanism, such as a robotic arm 14, a light source 22, and an electronic camera 18. The robotic arm 14 supports a silicon wafer 10 that is to be inspected for non-uniform surface areas or regions. The light source 22 is preferably comprised of an electroluminescent panel suitably positioned to cast a substantially uniform field of light over the entire surface of the wafer 10. Depending upon the particular type of device used for the light source 22, a suitable diffuser 17 may also be used in association with the panel. The light panel 22 floods wafer 10 with light that is of substantially uniform intensity over its entire surface area, and since it is positioned within the field of view of camera 18, wafer 10 reflects the light generated by panel 22 directly into the CCD camera 18.

As previously illustrated in FIG. 1, wafer 10 includes resist-burned regions 11, patterned array regions 12, and specular regions 13. Specular regions 13 do not contain circuitry and usually appear as a mirrored finish when compared to the patterned array regions 12 and resist-burned regions 11, when viewed the naked eye. The regions 12 containing integrated circuits formed on the wafer typically appear somewhat darker than the specular regions 13. The resist-burn region 11 is characterized as a defective region of the wafer and presents a dulled or smoked appearance when compared to the specular region 13 and patterned regions 12.

The area of space illuminated by the electro-luminescent panel 22 normally exceeds that occupied by the wafer 10 to ensure uniform illumination of the entire upper surface thereof. The camera 18 is preferably a charge-coupled device (CCD) camera focused to view the entire upper surface of the wafer 10. The camera 18 is positioned outside the space between panels 22 and wafer 10, and at an angle relative to the wafer surface, so that no image of the camera is reflected from the surface of the wafer back into the camera to cause development of inaccurate image data.

Camera 18 includes a lens system 19 which provides the proper magnification/demagnification necessary to accomplish the desired detection sensitivity. When high magnification is needed for a higher level of sensitivity, the entire wafer surface may not be visible in a single field view (FOV). In that case, the camera may be mounted on a moving stage 30 providing both X and Y translations and/or angle (θ-ω) rotation to enable scanning of the surface of the wafer in several FOVs. Camera 18 also includes internal functional components that measure the intensity of light reflected from the surface of the wafer 10. More specifically, camera 18 measures the light reflected from each picture element (pixel) over the surface area of wafer 10, and generates an output signal on line 40 which represents in serial fashion the intensity of light received from each pixel of the viewed object.

As camera 18 focuses on the surface of wafer 10 and captures the reflected image from panel 22 (which may also be curved), it scans the surface area of the wafer, and the specular regions 13 and patterned array regions 12 develop zero order reflections of the light from the illuminating panel. However, as camera 18 scans resist-burned regions 11, light from panel 22 is scattered, and the intensity of the light reflected into the camera is of lesser intensity, and that area appears darker than that of the rest of the wafer. An analog-to-digital (A/D) converter 42 receives the analog output signal developed by camera 18 on line 40 and converts it to digital form for input via line 44 to an image processor 46 which processes the signals and develops image data which can be processed by a display processor 48 and displayed by a monitor 50. Such data can also be stored on a recording medium such as a disk recorder 52. The output of processor 46 can also be used to actuate an audible alarm 54 or a visual alarm 56 to alert an operator to the fact that a burned region has been encountered.

The system has two basic modes of operation: training and inspection. The training operation is to eliminate any irrelevant background outside the perimeter of the wafer and to establish the gray-level range of a good wafer.

Figure 6:
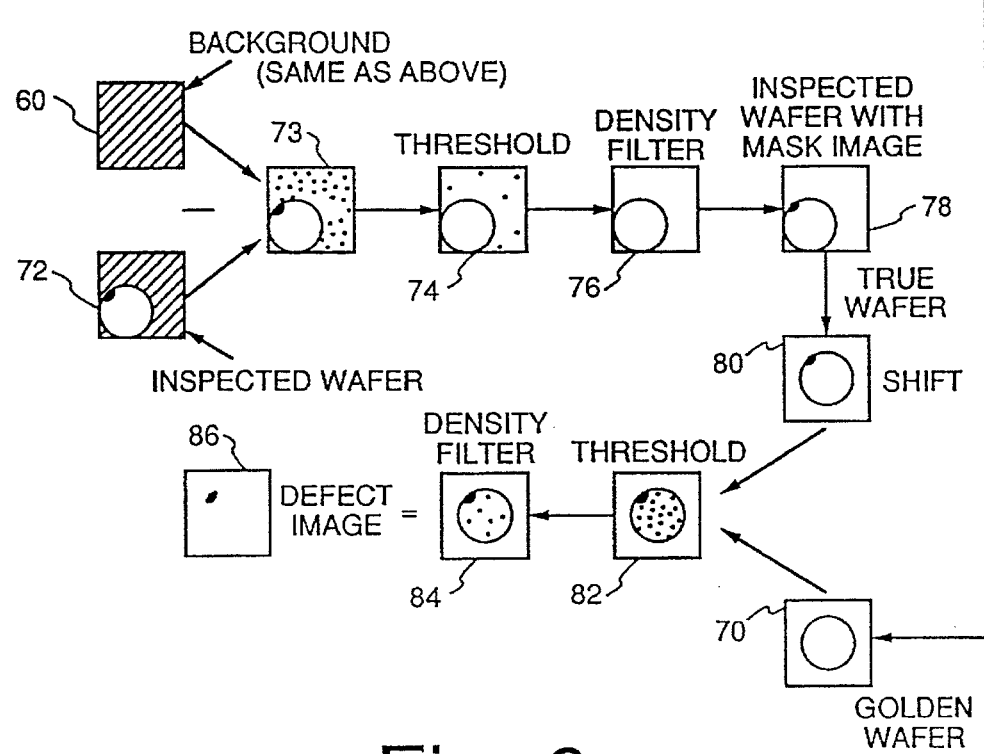
FIG. 6 is a pictorial diagram illustrating modes of use of the present invention.

To accomplish training, and as illustrated at the upper portion of FIG. 6, the system first grabs two images, i.e., a "background" image of light entering the camera with no wafer in its field of view as indicated at 60, and a "good" wafer image as indicated at 62. A good wafer image is one which is known to be free of resist-burn defects. The good wafer image data is then subtracted from the background image data as indicated at 62; the difference image is then thresholded at 64 and passed through a density filter 66, and is then eroded at 68 to establish a mask or good wafer image as indicated at 70. After that, the mask and good wafer image are used to produce a "golden wafer" image to be used later during the inspection mode.

When the system is operating in its inspection mode, the image 72 of the inspected wafer is compared with the previously stored background image 60 to develop a difference image 73 which is then thresholded at 74 and passed through a density filter 76. The filtered image is then masked with the original image of the inspected wafer to arrive at a "true wafer" image of the inspected wafer without the background. As indicated at 80, the "true wafer" image is then shifted in position to perfectly overlap the "golden wafer" image based on the center of mass of the two images. At this point, the two images 70 and 80 are compared pixel to pixel to produce a new "difference image" which is thresholded as indicated at 82, and passed through a density filter 84 to produce a final "defect" image in the form depicted at 86. The system constantly accumulates the statistics of the non-uniformities of the "defective" wafers and creates a model setting the rules to fail any subsequent wafers automatically when the system is switched into the inspection mode.

The system starts by classifying the pixels in the image by color (gray levels), establishes connectivities, and determines automatically the area of the wafer surface based on the circular periphery. Then, within the wafer surface area, all other color pixels are grouped together in blobs which are then classified by color, shape, dimension and position with respect to the wafer's center and its periphery. Various types of machine functions can then be associated with the corresponding types of non-uniformities found on the wafer. Not only can the machine be stopped automatically upon detection of non-uniformities, but it has the potential to diagnose the type of failure very effectively.

Although the present invention has been described above in terms of a specific embodiment specifically adapted for use in the inspection of silicon wafers, it is to be understood that the present invention can also be used to inspect other types of reflective surfaces where a high degree of uniformity is required. Such surfaces might include painted surfaces, polished surfaces, plated or anodized surfaces. In such application, a moving (relative to the object to be inspected) linear sensor (including a Time Delay Integration sensor) would be collecting the image, and image processing would be similarly done on a line-by-line basis. It is also anticipated that alterations and modifications of the preferred embodiment may become apparent to those skilled in the art following a reading of the above disclosure. It is therefore intended that the following claims be interpreted as covering all such applications, alterations and modifications as fall within the true spirit and scope of the invention.

What is claimed is:

1. Surface uniformity detection apparatus for analyzing the surface of a generally planar object, comprising:

means for receiving an object to be inspected, said object having a planar reflective surface intended to have a particular surface uniformity;

light source means providing a substantially areally uniform light output and being positioned to illuminate the reflective surface of said object to generate a reflected image indicative of the reflective characteristics of each pixel of the reflective surface;

image-capturing means for receiving said reflected image and for generating electrical signals corresponding to the reflectivity of each pixel of said reflective surface, said image-capturing means being positioned outside the space separating said light source means and said reflective surface, and disposed relative to said object and said light source means such that said light source means is disposed within the field of view of said image capturing means as reflected from said reflective surface; and processing means responsive to said electrical signals and operative to indicate whether or not said reflective surface has said particular surface uniformity.

2. Surface uniformity detection apparatus as recited in claim 1 wherein said light source means is a flat panel disposed in facing relationship to the reflective surface and is positioned to cover a predetermined portion of the reflected field of view of said image-capturing means.

3. Surface uniformity detection apparatus as recited in claim 2 wherein said panel occupies substantially all of the reflected field of view of said image-capturing means.

4. Surface uniformity detection apparatus as recited in claim 1 wherein said image-capturing means includes an electronic camera capable of generating an electrical output signal indicative of the light intensity of each pixel of an image of said reflective surface captured thereby.

5. Surface uniformity detection apparatus as recited in claim 4 wherein said image-capturing means is a charge-coupled device camera positioned to view substantially the entire reflective surface of an object being inspected.

6. Surface uniformity detection apparatus as recited in claim 1 wherein said image-capturing means includes an electronic camera positioned to capture an image of less than all of the reflective surface of an object to be inspected, said camera means including means for moving said camera relative to said reflective surface so that its field of view can be swept across the entire reflective surface.

7. Surface uniformity detection apparatus as recited in claim 1 wherein said image-capturing means has a field of view of less than the size of said object, and said means for receiving includes means for moving said object relative to said image-capturing means so that the entire reflective surface can be swept through the field of view of said image-capturing means.

8. Surface uniformity detection apparatus as recited in claim 1 wherein said image-capturing means generates an analog signal serially evidencing the reflective characteristics of each pixel of the reflective surface under inspection, and wherein said processing means includes:

an analog-to-digital converter for generating a digital signal indicative of the reflectivity of each pixel of the reflective surface under inspection;

image-processing means responsive to said digital signals and operative to generate an output from which an image of said reflective surface can be generated; and display means responsive to said output for generating a visual display of the reflectivity of said reflective surface.

9. Surface uniformity detection apparatus as recited in claim 8 wherein said light source means is a planar panel disposed in facing relationship to the reflective surface and positioned to cover a predetermined portion of the reflected field of view of said image-capturing means.

10. Surface uniformity detection apparatus as recited in claim 9 wherein said panel means occupies substantially all of the reflected field of view of said image-capturing means.

11. Surface uniformity detection apparatus as recited in claim 8 wherein said image-capturing means is a charge-coupled device camera positioned to view substantially the entire reflective surface of an object being inspected.

12. Surface uniformity detection apparatus as recited in claim 8 wherein said image-capturing means includes an electronic camera positioned to capture an image of less than all of the reflective surface of an object to be inspected, said camera means including means for moving said camera relative to said reflective surface so that its field of view can be swept across the entire reflective surface.

13. Surface uniformity detection apparatus as recited in claim 8 wherein said image-capturing means has a field of view of less than the size of said object, and said means for receiving includes means for moving said object relative to said image-capturing means so that the entire reflective surface can be swept through the field of view of said image-capturing means.

14. Surface uniformity detection apparatus as recited in claim 13 wherein said light source means is a planar panel disposed in facing relationship to the reflective surface and positioned to cover a predetermined portion of the reflected field of view of said image-capturing means.

15. A method of inspecting planar objects for surface uniformity, comprising the steps of:

receiving an object to be inspected, said object having a planar reflective surface intended to have a particular surface uniformity;

illuminating the reflective surface of said object with a light source having a substantially areally uniform light output to generate a reflected image indicative of the reflective characteristics of each pixel of the surface;

receiving said reflected image using an image-capturing means positioned outside the space separating said light source and said reflective surface, said image-capturing means being disposed relative to said planar object and said light source such that said light source is disposed within the field of view of said image capturing means as reflected from said reflective surface;

generating electrical signals corresponding to the reflectivity of each pixel of said surface;

processing said electrical signals; and using the processed electrical signals to indicate the degree of reflective uniformity of said surface.

16. A method of inspecting planar objects for surface uniformity as recited in claim 15, wherein said light source is a flat light panel disposed in facing relationship to said reflective surface and positioned to cover a predetermined portion of the reflected field of view of said image capturing means.

17. A method of inspecting planar objects for surface uniformity as recited in claim 16, wherein said light panel occupies substantially all of the reflected field of view of said capturing means.

18. A method of inspecting planar objects for surface uniformity as recited in claim 16 wherein said capturing means includes an electronic camera capable of generating an electrical output signal indicative of the light intensity of each pixel of an image of said reflective surface.

19. A method of inspecting planar objects for surface uniformity as recited in claim 18 wherein said capturing means is a charge-coupled device camera positioned to view substantially the entire reflective surface of the object being inspected.

20. A method of inspecting planar objects for surface uniformity as recited in claim 16 wherein said capturing means includes an electronic camera positioned to capture an image of less than all of the reflective surface of the object to be inspected, and further including the step of moving said camera relative to said reflective surface so that its field of view can be swept across the entire reflective surface being inspected.

21. A method of inspecting planar objects for surface uniformity as recited in claim 16 wherein said capturing means has a field of view of less than the size of said object, and further including the step of moving said object relative to said light-receiving means so that the entire reflective surface can be swept through the field of view of said capturing means.

22. A method of inspecting planar objects for surface uniformity as recited in claim 16 wherein said light-receiving means generates an analog signal serially evidencing the reflective characteristics of each pixel of the surface under inspection, and the step of processing further includes:

generating a digital signal indicative of the reflectivity of each pixel of the surface under inspection;

using the digital signals to generate an output from which an image of said surface can be generated; and generating a visual display of the areal reflectivity of said surface.

* * * * *

UNITED STATES PATENT AND TRADEMARK OFFICE
CERTIFICATE OF CORRECTION

PATENT NO. : 5,640,237
DATED : June 17, 1997
INVENTOR(S) : Paul Esrig and Eric James Hansotte It is certified that error appears in the above-identified patent and that said Letters Patent is hereby corrected as shown below:

On the title page, item [54], and Column 1,

In the title of the patent "surafaces" should be correctly spelled --surfaces--.

Signed and Sealed this

Eleventh Day of May, 1999

Attest:

Q. TODD DICKINSON

*Attesting Officer*     *Acting Commissioner of Patents and Trademarks*